United States Patent
Fu

(10) Patent No.: US 10,864,240 B2
(45) Date of Patent: Dec. 15, 2020

(54) PHARMACEUTICAL COMPOSITION FOR TREATING SKIN WOUNDS AND A METHOD OF TREATING SKIN WOUNDS USING THEREOF

(71) Applicant: Yuanqiao Fu, Shanghai (CN)

(72) Inventor: Yuanqiao Fu, Shanghai (CN)

(*) Notice: Subject to any disclaimer, the term of this patent is extended or adjusted under 35 U.S.C. 154(b) by 0 days.

(21) Appl. No.: 16/204,352

(22) Filed: Nov. 29, 2018

(65) Prior Publication Data

US 2019/0125815 A1 May 2, 2019

Related U.S. Application Data

(63) Continuation of application No. PCT/CN2017/085443, filed on May 23, 2017.

(51) Int. Cl.
| | | |
|---|---|---|
| *A61K 9/14* | (2006.01) | |
| *A61K 36/324* | (2006.01) | |
| *A61K 36/756* | (2006.01) | |
| *A61K 36/87* | (2006.01) | |
| *A61K 36/898* | (2006.01) | |
| *A61K 47/10* | (2017.01) | |
| *A61K 47/20* | (2006.01) | |
| *A61K 47/22* | (2006.01) | |
| *A61K 36/744* | (2006.01) | |
| *A61P 17/02* | (2006.01) | |
| *A61K 31/165* | (2006.01) | |
| *A61K 31/7036* | (2006.01) | |
| *A61K 36/232* | (2006.01) | |
| *A61K 36/328* | (2006.01) | |
| *A61K 36/481* | (2006.01) | |
| *A61K 36/484* | (2006.01) | |
| *A61K 36/537* | (2006.01) | |
| *A61K 36/539* | (2006.01) | |
| *A61K 36/65* | (2006.01) | |
| *A61K 36/71* | (2006.01) | |
| *A61K 36/889* | (2006.01) | |
| *A61K 45/06* | (2006.01) | |

(52) U.S. Cl.
CPC ......... *A61K 36/324* (2013.01); *A61K 31/165* (2013.01); *A61K 31/7036* (2013.01); *A61K 36/232* (2013.01); *A61K 36/328* (2013.01); *A61K 36/481* (2013.01); *A61K 36/484* (2013.01); *A61K 36/537* (2013.01); *A61K 36/539* (2013.01); *A61K 36/65* (2013.01); *A61K 36/71* (2013.01); *A61K 36/744* (2013.01); *A61K 36/756* (2013.01); *A61K 36/87* (2013.01); *A61K 36/889* (2013.01); *A61K 36/898* (2013.01); *A61K 45/06* (2013.01); *A61K 47/10* (2013.01); *A61K 47/20* (2013.01); *A61K 47/22* (2013.01); *A61P 17/02* (2018.01); *A61K 2236/33* (2013.01)

(58) Field of Classification Search
None
See application file for complete search history.

(56) References Cited

U.S. PATENT DOCUMENTS

| | | | |
|---|---|---|---|
| 4,855,294 A | 8/1989 | Patel et al. | |
| 9,289,459 B2* | 3/2016 | Lazdunski | A61K 36/537 |
| 2009/0062244 A1* | 3/2009 | Schwarz | A61K 9/0014 514/170 |
| 2013/0071450 A1* | 3/2013 | Copp-Howland | A61K 9/0009 424/400 |
| 2014/0120190 A1* | 5/2014 | Wei | A61K 8/97 424/771 |

FOREIGN PATENT DOCUMENTS

| | | | |
|---|---|---|---|
| CN | 1116539 A | | 2/1996 |
| CN | 1795897 A | | 7/2003 |
| CN | 101773511 A | | 7/2010 |
| CN | 101874809 A | | 11/2010 |
| CN | 102670690 A | * | 9/2012 |
| CN | 102178809 A | | 11/2012 |
| CN | 103622886 A | | 3/2014 |
| CN | 103877388 A | | 6/2014 |
| CN | 104984383 A | | 10/2015 |
| CN | 105560331 A | | 5/2016 |
| CN | 105833279 A | | 8/2016 |
| JP | 2010-195706 A | | 9/2010 |
| WO | 2005/079818 A1 | | 9/2005 |

OTHER PUBLICATIONS

Santus G. et al. Transdermal Enhancer Patent Literature J of Controlled Release 25(1-2)1-20, May 1993. (Year: 1993).*
Williams A. et al. Penetration Enhancers Advanced Drug Delivery Reviews 56:603-618, 2004. (Year: 2004).*
Luo X.H., A study on the percutaneous absorption in vitro of Tanshinone IIA Danshinone IIA, Master Graduation Thesis, ZheJiang University (2007) (see English abstract).
Thou et al., "Nursing progress in adjuvant therapy with traditional Chinese medicine for residual burns," Journal of Nursing Science, 25 (22) (2010) (see English abstract).
Luo X.H.: A study on the percutaneous absorption in vitro of Tanshinone IIA, 20 Industrial Pharmacy citation: Pan. W. S.: Industrial Pharmacy, 2006 (see English abstract).

* cited by examiner

*Primary Examiner* — Ralph J Gitomer
(74) *Attorney, Agent, or Firm* — Morgan, Lewis & Bockius LLP

(57) ABSTRACT

The invention generally relates to a liquid topical pharmaceutical composition used in treating various skin wounds. The composition is characterized by strong moisture absorption and retention capabilities and being able to quickly seal the wound. The composition can resist oxidation, effectively inhibit bacteria and sterilization, protect germinal cells from further damage, eliminate wound swelling and promote wound healing. The pharmaceutical composition can be widely used in the treatment of burn, skin abrasion, laceration, infectious skin ulcer and wound exposure, save dressing and be used in a convenient and highly effective way.

16 Claims, 1 Drawing Sheet

PHARMACEUTICAL COMPOSITION FOR TREATING SKIN WOUNDS AND A METHOD OF TREATING SKIN WOUNDS USING THEREOF

CROSS REFERENCE TO RELATED APPLICATIONS

This application claims the benefit of International Application No. PCT/CN2017/085443, filed May 23, 2017, which claims the benefit of Chinese Application Serial No. 201610369784.4, filed on May 30, 2016, the contents of which are hereby incorporated by reference herein in their entireties.

TECHNICAL FIELD

The present invention generally relates to a liquid topical pharmaceutical composition for the treatment of various wounds in human skin. The invention belongs to the surgical field of combined traditional Chinese and western medicine.

BACKGROUND

Repairing and healing of various skin wounds in human is a complex pathophysiological process. Slight and fine wounds undergo wound bleeding or exudation, dry scab, and healing under scab. Most of the relatively large or special skin wound (such as burns), after the injury, would experience exudation, infection, necrotic tissue clearance, infection control, wound exudation reduction, scabbing or wound coverage by biomaterial materials and wound healing of scar.

During the complex healing process in skin wounds, in addition to systemic treatment, one of the most important steps in wound treatment is the choosing of medicine for wounds. Currently there are various pharmaceutical preparations for treating skin wounds, which generally consist of suspensions, ointment, disinfectant and film forming agent. Those skilled in the art will appreciate that, although these types of wounds medications are effective, there are certain limitations existing in clinical treatment of skin wounds.

As mentioned above, among the applicable pharmaceutical preparations for treating skin wounds, for example, when a suspension is used, a large quantity of dressing is required to wrap the wounds, and the dressing would often stick to the wound surface after drying of the pharmaceutics, which makes new tissue tearing in wounds and causes bleeding during dressing replacing, prolongs the time of dressing replacing and increases the workload of medical staffs. For example when an ointment is used, the ointment would be incompatible with the wound exudation. Ointment is easy to flow in the case of more exudation of the wound surface, and also causes the adhesion between the dressing and wounds, which makes it difficult for dressing replacing. Film forming spray could seal the wounds better, however could not quite resolve the problem of the adsorption of wound exudation, therefore easily produces submembrane empyema.

The Chinese medicine believes that, "the river protects the grass and wood, and the Qi and blood protect the skin". The repairment of skin wound requires sufficient support from Qi and blood of human body, just as the grass and wood can't live without water and soil. Chinese medicine Astragali Radix, Angelicae Sinensis Radix, Salviae Miltiorrhizae Radix et Rhizoma and Paeoniae Radix Rubra are beneficial for the Qi, activate the blood, eliminate swelling and relieve pain, therefore the skin grows when Qi and blood are circulating.

Coptidis Rhizoma, Scutellariae Radix, Phellodendri Chinensis Cortex and Gardeniae Fructus are from the famous ancient prescription "Coptidis Decoction for Detoxification", which is recorded in Ge Hong's "Handbook of Prescriptions for Emergency" in East Jin dynasty and Wang Tao's "Medical Secrets from the Royal Library" in Tang dynasty, and usually internally used for treatment of various sores, ulcer and fire-toxicity by later physicians. It is frequently seen in the modern medical journals that Coptidis Rhizoma, Scutellariae Radix and Phellodendri Chinensis Cortex are fried or mixed with sesame oil and dressed to the wounds of burns and scalds. All the pains, itches and sores belong to the heart, and Scutellariae Radix purges fire of lung heat from the upper energizer, Coptidis Rhizoma purges fire of heart and stomach heat from the upper middle energizer, and Phellodendri Chinensis Cortex purges the kidney fire from the lower energizer. According to "the meaning of medicines", Phellodendri Chinensis Cortex purges fires everywhere from the top to the heels of feet and from the skin to the bone marrow, and Gardeniae Fructus purges fire of all three energizers. In that case, the fire-toxicity all over the body could be reduced to the end of the flow and there will be no burst sore. Modern researches have found that this decoction has the functions of degrading endotoxin, modulating immunoresponse, protecting brain, liver, kidney and intestinal mucosa and capillary and anti-apoptosis, and anticoagulant and anti-thrombosis.

Ampelopsis Radix is heat-clearing and detoxifying; Ilex purpurea Hassk is heat-clearing and detoxifying; astringing dampness and furuncle, and blood-cooling and blood-stanching; Bletillae Rhizoma is astringing dampness and furuncle; Glycyrrhizae Radix et Rhizoma harmonizes the herbs and is detoxifying and anti-inflammation, together with Astragali Radix, Angelicae Sinensis Radix, Salviae Miltiorrhizae Radix et Rhizoma and Paeoniae Radix Rubra, nourishes living cells of wounds Olibanum tends to promote Qi and open orifices and Myrrhaa tends to regulate blood and remove blood stasis. Olibanum and Myrrha have spicy dispersions and are important medicines for deportation of Qi stagnation and blood stasis. By circulating Qi and activating blood, swellings of big sores can be eliminated, so as to promote repairment of the local injuries. The swelling elimination and tissue regeneration functions of Olibanum and Myrrha can hardly be replaced by ordinary medicines.

Draconis Sanguis relieves blood pain and is a great medicine for blood harmonization. It specifically and greatly works in blood aspect, while Olibanum and Myrrha are mainly for blood illness, but they also work in Qi aspect. Draconis Sanguis is an important medicine to remove blood stasis and produce new blood. It mainly works in eliminating blood accumulation, treating metal-inflicted wound, killing pain, which is immediately effective when applied alone, or works better in removing blood stasis and activating blood when applied together with Olibanum and Myrrha. These three medicines can stop bleeding without leaving stasis and active blood so as to stop the pain, therefore they are considered as the three musketeers in blood illnesses, and wherever there is blood stasis, they can activate the blood and kill the pain. Catechu can remove the scab in addition to antibacterial and restraining functions.

There are dozens of medicinal materials for the treatment of the sore department recorded in the traditional Chinese medicine literature, and the above-mentioned sixteen kinds of Chinese medicinal materials are scattered in various prescriptions, which are only used as a component for the preparation of soups, powder (powders) and ointments. The limitations of these dosage forms in the treatment of burn wounds have been previously described.

In fact, an ideal wound medicine should be characterized as easing pain, fast wound sealing, absorbing wound exudation, reducing exudation, facilitating drainage, protecting wound area, promoting the growth of epithelial cell on wound area, broad and strong antibacterial effect, no production or low production of drug-resistant strain, toxin-free, few side-effects and few scars after wound healing. Therefore, the problem to be solved by the present invention is to find a convenient and highly efficient topical fluid pharmaceutical composition to treat various skin wounds, with the use of important raw materials and the combination of Chinese and Western medical ideas, and with ideas different from the past, to prepare the pharmaceutical composition using a specific method, so as to meet the requirements for an ideal wound preparation as far as possible.

SUMMARY OF THE INVENTION

This invention firstly emphasizes that an important component in the pharmaceutical composition of the present invention consists of glycerol, 1,2-propanediol, water-soluble Laurocapram or decyl methyl sulfoxide and water in a specific ratio. When used alone to treat various skin wounds, the important component could rapidly seal the wound area, absorb wound exudation, forms a transparent thin scab and resist the invasion of outside bacteria. When used in fine combination with a selection of pharmaceutical composition, they present a lot of ideal therapeutic effects! The biggest characteristics of the present invention are the important component and the specific ratio thereof.

Human body is an organism, whose periphery is fully covered by skins, and achieves metabolism and life maintenance through exchange materials with outside environment through blood circulation and body fluid exchange, which makes the minimal unit of the organism, i.e. every living cell exchange materials with outside in a completely closed and relatively constant environment. Skin injuries due to various reasons will cause the exposure of tissue cells that are previously protected by the skin and the "disaster" in local injured area. The body will recruit limited forces to the injured part to do emergency rescue, which leads to a series of pathophysiological alterations in the injured area. Because of the limited defective force the body could mobilize and the large wound area, the body has to rely on the outside medical aids. When facing the multiple skin wounds, doctors will firstly make the wound area restore the completely sealed state rapidly and be isolated from the surrounding air, then reverse the pathological alterations in the wound area such as hemostasis, anti-exudation, swelling subsidence and sterilization to promote the physiological repairment of wounds so that the multiple skin wounds could overcome the "disaster" smoothly and restore the normal states. The referred "the first priority in treating various skin wounds is to seal the wounds rapidly and completely" has been emphasized in none of the current literatures. It is due to the thorough observation and thinking of this statement, the inventor has performed serious practice repeatedly, and found out and selected glycerol, 1,2-propanediol, water-soluble Laurocapram or decyl methyl sulfoxide and a small amount of water in a specific ratio to be the basic medicine matrix of the pharmaceutical composition of the present invention, and formed pharmaceutical composition by accompanying selected Chinese medicinal herbs in order to thoroughly excavate the functions of four substances that constitute the basic medicine matrix, and achieved the present invention. The multiple skin wounds cannot be dressed with obvious stimulating medicines that cause re-injury of the tissue cell in wounds. The basic medicine matrix in this invention can not only fulfill the above-mentioned requirements, but also extract the effective medicinal ingredients of Chinese medicinal herbs to absorb water-dampness, stop exudation, promote penetration, make thin scabs, activate Qi and blood, dredge collateral, provide nutrition and promotes regeneration. All of the above are beneficial actions to promote wound healing and reduce scars.

The invention discloses a pharmaceutical composition for treating various skin wounds, wherein the important components of the present pharmaceutical composition comprises glycerol, 1,2-propanediol, water-soluble Laurocapram or decyl methyl sulfoxide, and water in a specific ratio, wherein the glycerol is present in the composition in an amount of 80% to 90% by volume.

In certain Examples, the 1,2-propanediol is present in the composition in an amount of 6% to 15% by volume; the water-soluble Laurocapram is present in the composition in an amount of 0.2% to 2% by volume, preferably in an amount of 0.6% to 1% by volume, more preferably in an amount of 0.2% to 0.5% by volume; the decyl methyl sulfoxide is present in the composition in an amount of 1% to 4% by volume, preferably in an amount of 1% to 3% by volume, and more preferably in an amount of 1% to 1.5% by volume; the water is present in the composition in an amount of 3% to 8% by volume, preferably in an amount of 3% to 5% by volume, and more preferably in an amount of 3% to 4% by volume.

One Example of the present invention discloses a pharmaceutical composition for treating various skin wounds and the important components thereof, wherein the important components consist of 80%-90% of glycerol by volume, 6%-15% of 1,2-propanediol by volume, 0.2%-2% of water-soluble Laurocapram by volume, or 1%-4% of decyl methyl sulfoxide by volume and 3%-8% of water by volume in the final pharmaceutical composition.

One specific Example of the present invention discloses the important component of a pharmaceutical composition for treating various skin wounds, when in alone treats sterile wound area, wherein the important components consist of 83.5% of glycerol by volume, 10% of 1,2-propanediol by volume, 0.5% of water-soluble Laurocapram by volume, and 6% of water by volume in the final pharmaceutical composition.

In certain specific Examples, the important components of the pharmaceutical composition described herein for treating various skin wounds consist of glycerol, preferably medical analytical pure glycerol (glycerol, glycerin, density 1.236 g/mL, weighted 628 g for 500 mL, molecular formula $C_3H_8O_3$, molecular weight 92.09, purity≥99%), 1,2-propanediol (1,2-Propanediol, molecular formula $C_3H_8O_2$, molecular weight 76.09, purity≥99%), water-soluble Laurocapram, and water in a specific ratio, wherein glycerol is 80%-90%, 1,2-propanediol is 6-15%, calculated by final volume. It takes full advantage of the two components being liquid form and moisture absorption and retention, which absorbs wound exudation and meanwhile keeps the wound from over drying.

The pharmaceutical composition described herein for treating various skin wounds comprises Laurocapram (Laurocapram, molecular formula $C_{18}H_{35}NO$, molecular weight 281.48, analytical purity>98%, relative density (20° C.) 0.906-0.926, neutral in pH), wherein the oil-soluble azone is modified to become water-soluble azone and is the complex of decyl methyl sulfoxide and pyrrolidone and a colorless, transparent, viscous liquid. It has obvious transdermal effect on the effective components of hydrophilic agents, which makes interaction between the skin cuticle and lipid, reduces temperature of the lipid phase transfer of the effective substance into the cuticle gap and increases the fluidity, which thereby reduces the diffusion resistance of the agents or active additives in the cuticle, and plays a strong role in enhancing the penetrating effect.

Water-soluble Laurocapram can effectively increase the penetration and absorption effects of the agents in the composition, lead to inhibition and elimination of the disease causing bacteria not only on the surface but also in the deep layer of the wounds, adequately exert the therapeutic function of agents and reduce the dosage of agents. In certain Examples, the content of water-soluble Laurocapram is preferably 2-20 mL/L, more preferably 6-10 mL/L, and most preferably 2-5 mL/L. In certain specific Examples, the water-soluble Laurocapram is pharmaceutical grade water-soluble Laurocapram.

In certain Examples, because of the similar effect, Laurocapram can be replaced by decyl methyl sulfoxide, wherein the content of decyl methyl sulfoxide is preferably 10-40 mL/L, more preferably 10-30 mL/L and most preferably 10-15 mL/L. In certain specific Examples, the decyl methyl sulfoxide is preferably pharmaceutical grade decyl methyl sulfoxide.

Water is a natural good solvent in the important components of the pharmaceutical composition described herein for treating various skin wounds. Then effects of containing water are: mixture of propanediol and water in certain ratio can extent the hydrolysis of certain agents, increase the stability thereof and prolong the validity period of the composition. In addition, high concentration of glycerol has strong moisture absorption capability, adding some amount of water helps balancing the strong moisture absorption capability. Hydrated glycerol can enhance the solubility of the pharmaceutically effective components in Chinese medicinal herbs under high temperature and high pressure. The content of water is preferably 30-80 mL/L, more preferably 30-50 mL/L and most preferably 30-40 mL/L.

In specific usage, the applicant has found that applying the pharmaceutical composition combined with the important components of the pharmaceutical composition in specific ratio and pharmaceutically effective components of selected Chinese medicine formulations onto the wound area can quickly seals the wound and forms a layer of transparent scab on the wound, effectively prevent and treat wound infection, eliminate wound edema, stop wound exudation, reduce the physical consumption of the patients, can resist the free radicals, protects wound area, nourish the germinal cells in the wound to grow hair and repair wound, and make the wound heal more quickly under the scab, for example there is usually little scar left in the II degree burn wounds.

In the pharmaceutical composition of present invention, there are raw materials of Chinese medicinal herbs:

The pharmaceutical composition of present invention further comprises at least one of the Astragali Radix, Angelicae Sinensis Radix, Salviae Miltiorrhizae Radix et Rhizoma and Paeoniae Radix Rubra, wherein the pharmaceutically effective components in at least one of the Astragali Radix, Angelicae Sinensis Radix, Salviae Miltiorrhizae Radix et Rhizoma and Paeoniae Radix Rubra is extracted by hydrated glycerol under high temperature and high pressure.

Astragali Radix

Astragali Radix comprises multiple chemically effective components which mainly comprise saponins, flavonoids, polysaccharides, amino acids and trace elements, etc. and has effects of tonifying Qi and lifting yang, stimulating saliva and nourishing blood, pus draining and toxin expelling, and promoting wound healing and tissue regeneration. The content of Astragali Radix in the composition is preferably 10-30 g/L, more preferably 10-20 g/L, and most preferably 10-15 g/L.

Angelicae Sinensis Radix

Angelicae Sinensis Radix comprises volatile oil, angelica lactone, ferulic acid, nicotinic acid, succinic acid, β-glucosterol, Daucosterol, monosaccharide, polysaccharide, phospholipid, various amino acids and inorganic elements, etc. and has the effects of tonifying and activating blood, regulating menstruation and alleviating pain, detoxifying and swelling eliminating, tonifying deficiency and removing stasis, nourishing Yin and blood and moisturizing skin and hair. The content of Angelicae Sinensis Radix in the composition is preferably 5-20 g/L, more preferably 5-10 g/L, and most preferably 6-8 g/L.

Salviae Miltiorrhizae Radix et Rhizoma

Salviae Miltiorrhizae Radix et Rhizoma comprises effective components as tanshinone, salvianolic acid, and baicalin and has the effects of anti-oxidation, anti-bacteria, activating blood and promoting menstruation, removing stasis, cooling blood and relieving pain, draining pus and relieving pain, forming flesh and regenerating tissue and promoting wound healing. The content of Salviae Miltiorrhizae Radix et Rhizoma in the composition is preferably 5-20 g/L, more preferably 5-15 g/L, and most preferably 8-10 g/L.

Paeoniae Radix Rubra

Paeoniae Radix Rubra comprises paeoniflorin, peonine, paeonol, catechin, ethyl gallate and volatile oil, etc. Paeoniae Radix Rubra can resist myocardial ischemia, improve blood microcirculation, inhibit platelet aggregation, anti-thrombotic formation, has analgesic, antispasmodic, live-protecting, anti-inflammatory and anti-bacterial effects, and has inhibitory effects on *Staphylococcus aureus* and *Pseudomonas aeruginosa*, fungi, herpes virus and enterovirus. The content of Paeoniae Radix Rubra in the composition is preferably 5-20 g/L, more preferably 5-15 g/L, and most preferably 8-10 g/L.

The pharmaceutical composition described herein may further comprises at least one of Coptidis Rhizoma, Scutellariae Radix, Phellodendri Chinensis Cortex and Gardeniae Fructus. The pharmaceutically effective components from at least one of the Coptidis Rhizoma, Scutellariae Radix, Phellodendri Chinensis Cortex and Fructus gardenia are extracted by hydrated glycerol under high temperature and high pressure.

Coptidis Rhizoma

Coptidis Rhizoma comprises various isoquinoline alkaloids and berberine. It can eliminate endotoxins, can resist *Staphylococcus aureus* and *Escherichia coli*, and has the effects of clearing heat and drying dampness and purging fire and detoxifying. For burns, topical administration of Coptidis Rhizoma decoction not only can resist infection, but also reduce exudation and promote scab formation. The content of Coptidis Rhizoma in the composition is preferably 5-20 g/L, more preferably 5-10 g/L, and most preferably 6-8 g/L.

Scutellariae Radix

Scutellariae Radix mainly comprises flavonoids, such as baicalein, wogonin, wogonoside, and comprises volatile oil, saccharides of amino acids. Scutellariae Radix has strong antibacterial activity and obvious inhibitory effects on *Staphylococcus aureus, Hemolytic streptococcus, Escherichia coli* and *Pseudomonas aeruginosa*, as well as anti-inflammatory and anti-oxidative effects. The content of Scutellariae Radix in the composition is preferably 5-20 g/L, more preferably 5-10 g/L, and most preferably 6-8 g/L.

Phellodendri Chinensis Cortex

Phellodendri Chinensis Cortex mainly comprises berberine, phellodendrine, obakunone and obakulactone. The Chinese medicine think Phellodendri Chinensis Cortex is good for toxic heat and sore. Phellodendri Chinensis Cortex has a significant inhibitory effect on *Staphylococcus aureus, Hemolytic streptococcus, Escherichia coli* and *Pseudomonas aeruginosa*. The content of Phellodendri Chinensis Cortex in the composition is preferably 5-20 g/L, more preferably 5-10 g/L, and most preferably 6-8 g/L.

Gardeniae Fructus

Gardeniae Fructus mainly comprises flavonoids such as iridoid geniposide, saffron and rutin etc., and has effects of purging fire and relieving restlessness, clearing heat and dampness, cooling blood and detoxification, and relieving swelling and pain for topical administration, as well as relatively strong anti-bacterial effects on *Staphylococcus aureus* and *Hemolytic* streptococcus. The content of Gardeniae Fructus in the composition is preferably 5-20 g/L, more preferably 5-10 g/L, and most preferably 6-8 g/L.

The pharmaceutical composition described herein may also contain at least one of Ampelopsis Radix, Ilex purpurea Hassk, Bletillae Rhizoma and Glycyrrhizae Radix et Rhizoma. The pharmaceutically effective components from at least one of the Ampelopsis Radix, Ilex purpurea Hassk, Bletillae Rhizoma, and Glycyrrhizae Radix et Rhizoma are extracted by hydrated glycerol under high temperature and high pressure.

Ampelopsis Radix

The major components in Ampelopsis Radix are gallic acid, tartaric acid, sitosterol, chrysophanol and mucosubstance, and have effects of clearing heat and detoxifying, eliminating swelling and regenerating tissue. This product is bitter, cold, clearing and discharging. It has pungent taste and dispersing effect, promotes wound healing, forms flesh, and relieves pain. It also has obvious inhibitory effects on *Staphylococcus aureus, Pseudomonas aeruginosa* and *Escherichia coli*. Ampelopsis Radix is commonly known as "subsiding swelling" which has strong anti-infective effect even when used alone. The content of Ampelopsis Radix in the composition is preferably 5-20 g/L, more preferably 6-15 g/L, and most preferably 8-10 g/L.

Ilex purpurea Hassk The major components in Ilex purpurea Hassk are protocatechuic acid, protocatechuic aldehyde, condensed tannic acid, flavonoid and volatile oil. Ilex purpurea Hassk has effects of heat-clearing and detoxifying, blood-cooling and blood-stanching, and wound healing. Ilex purpurea Hassk has the functions of anti-inflamation, anti-bacteria, increasing coronary artery blood flow, anti-myocardial ischemia, forming protective eschar membrane on burn wound and preventing infection and exudation. It advantages like absorptivity and certain permeability without increasing the depth of the wound. The content of Ilex purpurea Hassk in the composition is preferably 5-20 g/L, more preferably 5-15 g/L, and most preferably 8-10 g/L.

Bletillae Rhizoma

The major components in Bletillae Rhizoma are benzyl, phenanthrene and the derivatives thereof, and a small amount of volatile oil mucosubstance. It has effects of astringing hemostasis and stanching blood, and eliminating swelling and regenerating tissue. Bletillae Rhizoma is used for treating chapped skin and scalds, absorbing would exudation, protecting wound and promoting wound healing. The content of Bletillae Rhizoma in the composition is preferably 5-20 g/L, more preferably 6-15 g/L, and most preferably 8-10 g/L.

Glycyrrhizae Radix et Rhizoma

Glycyrrhizae Radix et Rhizoma comprises more than 100 of flavonoids, more than 60 of triterpenoids, 18 amino acids, a variety of alkaloids, etc. It acts like glucocorticoid, has functions of anti-inflammation, anti-oxidation, modulating immunity and detoxification, and has effects of anti-virus, anti-bacteria, invigorating spleen and replenishing Qi, clearing heat and detoxifying, relieving pain and harmonizing medicines. The content of Glycyrrhizae Radix et Rhizoma in the composition is preferably 5-15 g/L, more preferably 6-12 g/L, and most preferably 8-10 g/L.

The pharmaceutical composition described herein may also contain at least one of Olibanum, Myrrha, Draconis Sanguis and Catechu. The pharmaceutically effective components from at least one of the Olibanum, Myrrha, Draconis Sanguis and Catechu are extracted by immersion method with 1,2-propanediol.

Olibanum

Olibanum mainly comprises resin, gum and volatile oil. Olibanum has analgesic and anti-inflammatory activities and has effects of activating blood, promoting Qi, relieving pain, eliminating swelling and regenerating tissue, and is an important medicine for treating toxins from ulcer, sore, carbuncle, deep-rooted carbuncle and furuncle. The content of Olibanum in the composition is preferably 3-10 g/L, more preferably 5-8 g/L, and most preferably 5-6 g/L.

Myrrha

Myrrha mainly comprises resin, gum and volatile oil. The water infusion agent has an inhibitory effect on the fungus, and is often paired with the Olibanum to play a role in activating blood and relieving pain, eliminating swelling and regenerating tissue and enhancing stasis-removing. Chinese medicine thinks that the new blood will not be generated until the blood stasis is cleared. The content of Myrrha in the composition is preferably 3-10 g/L, more preferably 5-8 g/L, and most preferably 5-6 g/L.

Draconis Sanguis

Draconis Sanguis comprises dracorhodin, dracorubin, resin acid, etc. It has effects of activating blood, anti-inflammatory and analgesic, promoting blood circulation, and promoting wound healing and regenerating tissue. The content of Draconis Sanguis in the composition is preferably 3-10 g/L, more preferably 5-8 g/L, and most preferably 4-5 g/L.

Catechu

Catechu comprises catechol, is anti-inflammatory and anti-bacterial (inhibition of gram positive and negative bacteria, inhibition of *Staphylococcus aureus*, enterococci, *Escherichia coli*, and anti-influenza virus), and has effects of activating blood and healing, stanching blood and regenerating tissue, astringing dampness and furuncle. The content of Catechu in the composition is preferably 3-10 g/L, more preferably 5-8 g/L, and most preferably 4-5 g/L.

The pharmaceutical composition described herein may further comprise antibiotics.

The antibiotics described herein comprise gentamicin and chloramphenicol.

In addition to the above ingredients, every 100 mL of the compositions of the present invention can be temporarily added by a group of antibiotics, such as: 80,000 units of gentamicin and 0.25 g of chloramphenicol (not limited to the two antibiotics, can also select another suitable group of antibiotics) and applied to the wound area after thorough shaking under the guidance of drug sensitivity test according to etiological diagnosis of wound infection for some cases of severe wound infections.

One Example of the present invention discloses the important component of a pharmaceutical composition for treating various skin wounds, wherein the pharmaceutical composition is made from the following raw materials based on w/v (Weight/volume) ratio: Astragali Radix 10-30 g/L, Angelicae Sinensis Radix 5-20 g/L, Salviae Miltiorrhizae Radix et Rhizoma 5-20 g/L, Paeoniae Radix Rubra 5-20 g/L, Coptidis Rhizoma 5-20 g/L, Scutellariae Radix 5-20 g/L, Phellodendri Chinensis Cortex 5-20 g/L, Gardeniae Fructus 5-20 g/L, Ampelopsis Radix 5-20 g/L, Ilex purpurea Hassk 5-20 g/L, Bletillae Rhizoma 5-20 g/L, Glycyrrhizae Radix et Rhizoma 5-15 g/L, Olibanum 3-10 g/L, Myrrha 3-10 g/L, Draconis Sanguis 3-10 g/L and Catechu 3-10 g/L, and glycerol 80%-90%, 1,2-propanediol 6%-15%, water-soluble Laurocapram 0.2%-2% or decyl methyl sulfoxide 1%-4% and water 3%-8% by final volume.

One Example of the present invention discloses the important component of a pharmaceutical composition for treating various skin wounds, wherein the pharmaceutical composition is made from the following raw materials based on w/v ratio: Astragali Radix 10-20 g/L, Angelicae Sinensis Radix 5-10 g/L, Salviae Miltiorrhizae Radix et Rhizoma 5-15 g/L, Paeoniae Radix Rubra 5-15 g/L, Coptidis Rhizoma 5-10 g/L, Scutellariae Radix 5-10 g/L, Phellodendri Chinensis Cortex 5-10 g/L, Gardeniae Fructus 5-10 g/L, Ampelopsis Radix 6-15 g/L, Ilex purpurea Hassk 5-15 g/L, Bletillae Rhizoma 6-15 g/L, Glycyrrhizae Radix et Rhizoma 6-12 g/L, Olibanum 5-8 g/L, Myrrha 5-8 g/L, Draconis Sanguis 5-8 g/L and Catechu 5-8 g/L, and glycerol 80%-90%, 1,2-propanediol 6%-15%, water-soluble Laurocapram 0.6%-1% or decyl methyl sulfoxide 1%-3% and water 3%-5% by final volume.

One Example of the present invention discloses the important component of a pharmaceutical composition for treating various skin wounds, wherein the final w/v ratio of the raw materials is Astragali Radix 10-15 g/L, Angelicae Sinensis Radix 6-8 g/L, Salviae Miltiorrhizae Radix et Rhizoma 8-10 g/L, Paeoniae Radix Rubra 8-10 g/L, Coptidis Rhizoma 6-8 g/L, Scutellariae Radix 6-8 g/L, Phellodendri Chinensis Cortex 6-8 g/L, Gardeniae Fructus 6-8 g/L, Ampelopsis Radix 8-10 g/L, Ilex purpurea Hassk 8-10 g/L, Bletillae Rhizoma 8-10 g/L, Glycyrrhizae Radix et Rhizoma 8-10 g/L, Olibanum 5-6 g/L, Myrrha 5-6 g/L, Draconis Sanguis 4-5 g/L and Catechu 4-5 g/L, and glycerol 80%-90%, 1,2-propanediol 6%-15%, water-soluble Laurocapram 0.2%-0.5% or decyl methyl sulfoxide 1%-1.5% and water 3%-4% by final volume.

One specific Example of the present invention discloses the important component of a pharmaceutical composition for treating various skin wounds, wherein the final w/v ratio of the raw materials is Astragali Radix 20 g/L, Angelicae Sinensis Radix 15 g/L, Salviae Miltiorrhizae Radix et Rhizoma 15 g/L, Paeoniae Radix Rubra 15 g/L, Coptidis Rhizoma 10 g/L, Scutellariae Radix 10 g/L, Phellodendri Chinensis Cortex 10 g/L, Gardeniae Fructus 10 g/L, Ampelopsis Radix 15 g/L, Ilex purpurea Hassk 15 g/L, Bletillae Rhizoma 15 g/L, Glycyrrhizae Radix et Rhizoma 12 g/L, Olibanum 8 g/L, Myrrha 8 g/L, Draconis Sanguis 6 g/L and Catechu 6 g/L, and glycerol 80%, 1,2-propanediol 14%, water-soluble Laurocapram 1% and water 5% by final volume.

One specific Example of the present invention discloses the important component of a pharmaceutical composition for treating various skin wounds, wherein the final w/v ratio of the raw materials is Salviae Miltiorrhizae Radix et Rhizoma 20 g/L, Phellodendri Chinensis Cortex 20 g/L, Ilex purpurea Hassk 20 g/L, Bletillae Rhizoma 15 g/L, Glycyrrhizae Radix et Rhizoma 15 g/L and Catechu 8 g/L, and glycerol 88.4%, 1,2-propanediol 8%, water-soluble Laurocapram 0.6% and water 3% by final volume.

One specific Example of the present invention discloses the important component of a pharmaceutical composition for treating various skin wounds, wherein the final w/v ratio of the raw materials is Astragali Radix 10 g/L, Angelicae Sinensis Radix 8 g/L, Salviae Miltiorrhizae Radix et Rhizoma 8 g/L, Paeoniae Radix Rubra 8 g/L, Coptidis Rhizoma 6 g/L, Scutellariae Radix 6 g/L, Phellodendri Chinensis Cortex 6 g/L, Gardeniae Fructus 6 g/L, Ampelopsis Radix 10 g/L, Ilex purpurea Hassk 10 g/L, Bletillae Rhizoma 10 g/L, Glycyrrhizae Radix et Rhizoma 8 g/L, Olibanum 5 g/L, Myrrha 5 g/L, Draconis Sanguis 4 g/L and Catechu 4 g/L, and glycerol 83.7%, 1,2-propanediol 12%, water-soluble Laurocapram 0.3% and water 4% by final volume.

Another aspect of the present invention discloses the preparation method of the pharmaceutical composition, wherein the preparation method comprises: finely select and measure proper amount of at least three of Astragali Radix, Angelicae Sinensis Radix, Salviae Miltiorrhizae Radix et Rhizoma, Paeonia lactiflora Pal, Coptidis Rhizoma, Scutellariae Radix, Phellodendri Chinensis Cortex, Gardeniae Fructus, Ampelopsis Radix, Ilex purpurea Hassk, Bletillae Rhizoma and Glycyrrhizae Radix et Rhizoma, add them into corresponding amount of distilled water mixed with corresponding amount of glycerol, heat the raw material-containing glycerol from separation layer for 10 min under steam pressure of 0.02 MPa and temperature of 105° C., filter out the dregs after cooling, make up the lost hydrated glycerol; finely select and measure proper amount of at least one of Olibanum, Myrrha, Draconis Sanguis and Catechu, add into corresponding amount of 1,2-propanediol, soak for 24 hr., filter out the dregs, make up the lost 1,2-propanediol; mix the glycerol containing effective components of raw materials and 1,2-propanediol containing effective components of raw materials with corresponding amount of water-soluble Laurocapram or decyl methyl sulfoxide, stir thoroughly, fill in bottles and sterilize.

In one specific Example of the present invention, the described preparation method comprises: finely select and measure proper amount of totally at least three medicines which contain at least one of Astragali Radix, Angelicae Sinensis Radix, Salviae Miltiorrhizae Radix et Rhizoma and Paeoniae Radix Rubra; at least one of Coptidis Rhizoma, Scutellariae Radix, Phellodendri Chinensis Cortex and Gardeniae Fructus; and at least one of Ampelopsis Radix, Ilex purpurea Hassk, Bletillae Rhizoma and Glycyrrhizae Radix et Rhizoma, add totally at least three medicines into corresponding amount of distilled water mixed with corresponding amount of glycerol, heat the raw material-containing glycerol from separation layer for 10 min under steam pressure of 0.02 MPa and temperature of 105° C., filter out the dregs after cooling, make up the lost hydrated glycerol; finely select and measure proper amount of at least one of Olibanum, Myrrha, Draconis Sanguis and Catechu, add into corresponding amount of 1,2-propanediol, soak for 24 hr, filter out the dregs, make up the lost 1,2-propanediol; mix the glycerol containing effective components of raw materials and 1,2-propanediol containing effective components of raw materials with corresponding amount of water-soluble Laurocapram or decyl methyl sulfoxide, stir thoroughly, fill in bottles and sterilize.

The effective components of Chinese medicinal herbs in composition of the present invention are extracted by solvent glycerol or 1,2-propanediol. Under room temperature, the effective components of Chinese medicinal herbs have low solubility in glycerol and precipitate slowly. The applicant has found that given proper pressure, temperature and certain time, the effective components of Chinese medicinal herbs have good solubility in glycerol by adding a small amount of water into glycerol. The boiling temperature of glycerol is 290° C. In practice, the hydrated glycerol is heated up to 105° C. by high pressure steam from separation layer and maintained for 10 min. The selection of such temperature and time is to maintain the chemical stability of glycerol and to dissolve the effective components of Chinese medicinal herbs ideally.

1,2-propanediol has relative low proportion in the common components of the composition, however, the amount used is enough as a solvent for soaking and extracting pharmaceutically effective components of Olibanum, Myrrha, Draconis Sanguis and Catechu in composition.

Following the principles of traditional Chinese medicine surgery of clearing heat and detoxicating, activating blood and removing swelling, removing putrefaction and promoting tissue regeneration, and astringing dampness and furuncle, with the thought of "complemented by clearing and dredging, nourished by dredging, balanced by nourishing and purging and treated by both dredging and nourishing", the present invention makes a new big prescription consisting four medicine matrixes with many varieties and light doses from Astragali Radix, Angelicae Sinensis Radix, Salviae Miltiorrhizae Radix et Rhizoma and Paeoniae Radix Rubra; from Scutellariae Radix, Phellodendri Chinensis Cortex and Gardeniae Fructus; from Ampelopsis Radix, Ilex purpurea Hassk, Bletillae Rhizoma and Glycyrrhizae Radix et Rhizoma; and from Olibanum, Myrrha, Draconis Sanguis and Catechu. With the addition of a basic medicine matrix capable of adsorbing dampness, keeping moisture, forming membrane and being solvent, the five medicine matrixes work together, with comprehensive theories and appropriate prescriptions, and create a new preparation, which is repeatedly and effectively used in clinical practice by the inventor.

With respect to structure of the prescription, macroscopically, the first medicine matrix herbs Astragali Radix, Angelicae Sinensis Radix, Salviae Miltiorrhizae Radix et Rhizoma, and Paeoniae Radix Rubra are part of monarch, nourishing Qi and blood and expelling toxins from within body; the second medicine matrix herbs Scutellariae Radix, Phellodendri Chinensis Cortex and Gardeniae Fructus are part of minister, clearing toxins and purging fire; the third medicine matrix herbs Ampelopsis Radix, Ilex purpurea Hassk, Bletillae Rhizoma, and Glycyrrhizae Radix et Rhizoma are part of assistant, astringing dampness and furuncle and removing swelling; the forth medicine matrix herbs Olibanum, Myrrha, Draconis Sanguis and Catechu are part of guide, promoting Qi, activating blood, dredging collateral, removing putrefaction and promoting tissue regeneration. Microscopically, the four medicine matrixes are four small prescriptions, each of which comprises four Chinese medicine herbs and forms corresponding monarch, minister, assistant and guide according to the function and property in the above mentioned order.

The invention also discloses the use of the pharmaceutical composition in preparation of topical medicine for treating various skin wounds.

In certain Examples, the various skin wounds do not comprise: skin ulcers caused by Mycobacterium tuberculosis infection or malignant tumor and acnes caused by imbalance of androgen secretion.

In certain specific Examples, the various skin wounds described herein comprise burn wound, scald wound, skin contusion wound, suture wound after incision, bedsore wound, skin infection wound and granulation tissue wound.

Beneficial Effect of the Invention

The beneficial effect of the present invention is to disclose a liquid topical pharmaceutical composition for treating various skin wounds in human. Using the pharmaceutical composition containing effective components of Chinese medicine raw material can rapidly and effectively seal wound, remove wound swelling, reduce or stop wound exudation. The pharmaceutical composition forms transparent thin scab with the preexisted wound exudation, protects wound basement and vital cells around from further injury, prevent and control wound infection, promote subcrustal healing of wound and maximize the reduction of scar formation. The pharmaceutical composition can be applied for topical administration in treating various skin wounds.

BRIEF DESCRIPTION OF THE DRAWINGS

FIG. 1 is a graph showing the product of pharmaceutical composition Formulation 3 of the present invention.

DETAILED DESCRIPTION

The present invention will be further described below by way of specific Examples and examples. Although specific terms are used hereinafter for the purpose of clarity, these terms are not intended to define or limit the scope of the invention.

As used herein, the term "medical" refers to the reagents with purities higher than 95%. The "medical glycerol" used in the Examples of the present invention is analytical grade medical glycerin, with density of 1.236 g/mL, weight 628 g for 500 mL, molecular formula $C_3H_8O_3$, molecular weight 92.09, purity≥99%; the purity of medical 1,2-propanediol≥99%.

As used herein, the term "pharmaceutical grade" refers to a chemical purity that can be used in medicines for human. The water-soluble Laurocapram herein is pharmaceutical grade.

As used herein, the term "treatment" refers to reverse, alleviate or inhibit the progress of the disease applied to, or one or more symptoms of the disease. As used herein, depending on the state of patients, the term also comprises disease prevention, including preventing the occurrence of disease or any other related symptom thereof, and alleviating the seriousness of a condition or any other symptom before.

As used herein, the term "hydrated glycerol" refers to a solvent mixed by glycerol and water in a specific ratio. In Examples of the present disclosure, the volume of glycerol is 80-90 parts, and the volume of water is 3-8 parts. The volume ratio between glycerol and water in "hydrated glycerol" used in specific Examples of the present disclosure is preferably 800:50, or 884:30, or 837:40, or 835:60.

The invention is further described in detail with reference to the specific Examples thereof, and various modifications of the invention in accordance with the invention. The methods of the following examples are routine methods unless otherwise stated.

EXAMPLES

Example 1: Preparation of the Pharmaceutical Composition

The pharmaceutical composition preparations 1-3 of the present invention is prepared according to proportions in table 1 and the following technical process.

The preparation process is:

1) Finely select and measure proper amount of Astragali Radix, Angelicae Sinensis Radix, Salviae Miltiorrhizae Radix et Rhizoma, Paeoniae Radix Rubra, Coptidis Rhizoma, Scutellariae Radix, Phellodendri Chinensis Cortex, Gardeniae Fructus, Ampelopsis Radix, Ilex purpurea Hassk, Bletillae Rhizoma and Glycyrrhizae Radix et Rhizoma as the compositional components in table 1, add them into corresponding amount of distilled water as in table 1 for the same preparation and mixed with corresponding amount of glycerol, heat the raw material-containing glycerol from separation layer for 10 min under steam pressure of 0.02 MPa and temperature of about 105° C., filter out the dregs after cooling, make up the lost hydrated glycerol;

2) Finely select and measure proper amount of Olibanum, Myrrha, Draconis Sanguis and Catechu as the compositional components in table 1, add them into corresponding amount of 1,2-propanediol as in table 1 for the same preparation, soak for 24 hr. to dissolve medicinal active ingredients, filter out the dregs, make up the lost 1,2-propanediol;

3) Mix the hydrated glycerol containing Chinese medicine juice and 1,2-propanediol with corresponding amount of distilled water and water-soluble Laurocapram as shown in table 1 for the same preparation, stir thoroughly, fill in bottles and sterilize.

The preparation process for Formulation 4 copies the above steps but without measuring Chinese medicine herbs.

TABLE 1

| Components | Composition quantity (in 1000 mL) | | | |
| --- | --- | --- | --- | --- |
| | Formulation 1 | Formulation 2 | Formulation 3 | Formulation 4 |
| glycerol | 800 mL | 884 mL | 837 mL | 835 mL |
| 1,2-propanediol | 140 mL | 80 mL | 120 mL | 100 mL |
| water-soluble Laurocapram | 10 mL | 6 mL | 3 mL | 5 mL |
| Distilled water | 50 mL | 30 mL | 40 mL | 60 mL |
| Astragali Radix | 20 g | — | 10 g | — |
| Radix Angelicae Sinensis | 15 g | — | 8 g | — |
| Salviae Miltiorrhizae Radix et Rhizoma | 15 g | 20 g | 8 g | — |
| Paeoniae Radix Rubra | 15 g | — | 8 g | — |
| Coptidis Rhizoma | 10 g | — | 6 g | — |
| Scutellariae Radix | 10 g | — | 6 g | — |
| Phellodendri Chinensis Cortex | 10 g | 20 g | 6 g | — |
| Gardeniae Fructus | 10 g | — | 6 g | — |
| Ampelopsis Radix | 15 g | — | 10 g | — |
| Ilex purpurea Hassk | 15 g | 20 g | 10 g | — |
| Bletilla striata | 15 g | 15 g | 10 g | — |
| Glycyrrhizae Radix et Rhizoma | 12 g | 15 g | 8 g | — |
| Olibanum | 8 g | — | 5 g | — |
| Myrrha | 8 g | — | 5 g | — |
| Draconis Sanguis | 6 g | — | 4 g | — |
| Catechu | 6 g | 8 g | 4 g | — |

In addition to the above ingredients, every 100 mL of the compositions of the present invention can be temporarily added by a group of antibiotics, such as: 80,000 units of gentamicin and 0.25 g of chloramphenicol (not limited to the two antibiotics, can also select another suitable group of antibiotics) and applied to the wound area after thorough shaking under the guidance of drug sensitivity test according to etiological diagnosis of wound infection for some cases of severe wound infections.

Example 2 Clinical Verification of Pharmaceutical Composition Formulation 4 for Treating Sutured Wound after Skin Incision Formulation 4 in table 1 is an important component in the pharmaceutical composition of the present invention, and consists of glycerol, 1,2-propanediol, water-soluble Laurocapram, and water in specific ratio. The traditional treatment after suture of skin incision wound is to cover the wound with 75% alcohol gauze. The following is the clinical comparative observation using pharmaceutical composition Formulation 4 of the present invention and using traditional alcohol dressing for treating sutured wound after skin incision.

1) General Information:

Totally 50 cases after aseptic operation were selected, aged between 20-60 years old, among which 40 men and 10 women were divided into treatment group and control group. The length of skin incision was more than 8 cm in average.

2) Treatment Method:

a. Treatment group: After suturing, cleansing and disinfection of the skin incision, apply Formulation 4 onto the wound stitch with cotton ball, cover the wound stitch with sterile gauze after 1-2 min and fix with adhesive tape. Apply Formulation 4 once on day 2 when change the wound dressing and again on day 7-8 after removing the suture in time to seal the stitch.

b. Control group: After suturing, cleansing and disinfection of the skin incision, dress the wound stitch with 75% alcohol gauze, cover with sterile gauze and fix with adhesive tape. Change the wound dressing on day 3, when there were signs of infection in a small number of cases, and change the dressing every day until the wound is healed.

3) Evaluation Criteria of Therapeutic Effect

Evaluate the therapeutic effect from day 3 after wound suture to day 7 after suture removing, according to the wound healing state and inflammatory response on the stitch.

a. Excellent healing: scab on wound stitches after 3 days, no or few exudation, little dressing stains on wound. 7 days after operation, wound healed at I grade and little inflammatory response on the stitch.

b. Good healing: little exudation on wound stitch after 3 days, obvious stains on wound dressing. The exudation gradually reduced after applying iodine and change the wound dressing every day for consecutive 3 days and the scab gradually formed on wound stitches. Usually the suture was removed 8-9 days after operation, wound healed at I grade and there was congestion and redness on stitches.

c. Poor healing: wound exudation on day 3 when changing the dressing on stitch, slightly damp dressing, redness on stitches and removing of sutures at intervals was required to facilitate the drainage of wound exudation. Change the dressing every day. Prolonged wound healing.

4) Treatment Results (See Table 2)

TABLE 2 clinical comparative observation and quantitation in treating sutured sterile wound after skin incision using pharmaceutical composition Formulation 4 of the present invention and using traditional 75% alcohol gauze dressing.

| group | Case number | Excellent healing 10 points | | Good healing 8 points | | Poor healing 3 points | | Expected score | Real score | Fine rate % |
|---|---|---|---|---|---|---|---|---|---|---|
| | | Case number | score | Case number | score | Case number | score | | | |
| Treatment group | 25 | 25 | 250 | | | | | 250 | 250 | 100 |
| Control group | 25 | 19 | 190 | 5 | 40 | 1 | 3 | 250 | 233 | 93.2 |

5) Discussion

The clinical comparative observation and quantitation result in table 2 showed that the therapeutic effect of pharmaceutical composition Formulation 4 of the present invention in treating sutured wound after skin incision is better than the traditional treating method which covers the sutured wound with 75% alcohol gauze. This is because the alcohol is volatile disinfectant although it kills bacteria. If 75% alcohol gauze is used for wound dressing, there will only be gauze left in a few hours after the alcohol gets fully volatilized. If the patient is not well cared for, the bacteria can easily invade the wound stitch from the edge of the gauze, causing varying degrees of wound infection. The components in pharmaceutical composition Formulation 4 of the present invention are mainly glycerol and 1,2-propanediol which are not volatile, and can rapidly and completely seal wound stitch after contacting it, absorb a small amount of exudation on wound stitch, form a transparent layer of scab by binding with proteins in the exudation, and protect the wound from the invasion of outside bacteria closely to make the wound stitch clean and dry and achieve good healing.

Example 3 Clinical Observation of the Wound in Burned Patients Treated with the Pharmaceutical Composition According to the pathophysiological healing mechanism of various skin injuries, the skin injuries caused by burns are the most serious, complex and representative one. The inventor illustrates the therapeutic examples of the invented pharmaceutical composition on skin wound treatment using burn wound as a model.

The principle of dealing and treating burns is early prevention and the treatment of shock. The important step in treating burns is the short course application of sufficient and highly effective antibiotics and treating burn wounds scientifically during early stage, therefore makes the wound tightly covered and reduces the wound exudation, i.e. reduces patient's physical consumption, keeps the wound dry, makes the broad-spectrum antibiotics reach the deep part of the wound, protects the residue epithelial germinal cells from free radicals, oxidation and apoptosis and promotes wound healing.

One pharmaceutical composition of the present invention for treating various skin wounds is designed according to the above requirements for treating wounds. The important components of composition is the matrix, selected mainly as concentrated glycerol and 1,2-propanediol and have high hygroscopicity and proper moisture retention. The matrix forms dry and not hard transparent scabs by binding with the water in wound exudation and amino acids above the plasma content, seals the wound rapidly so as to prevent the growth of bacterial in the air that fall into the wound after administration, and the bacteria cannot invade from the outside. At the meantime, because of the proper amount of Laurocapram or decyl methyl sulfoxide in the recipe, they can lead the effective medical ingredients in the formula with effects of antibacterial, nutritional, antioxidant and microcirculation to penetrate deep into the wound surface, thereby leading to the improvement of blood supply in wound tissue, blockage of the intestinal bacteria from reaching the wound by blood circulation, reduction of the early inflammation and re-injury on wounds and obtaining the ideal therapeutic effect of "both internal and topical repairments". This is the delightful finding of the inventor in the practice of the present invention. It is believed that this will play an important role in exploring the molecular mechanism and cytology of burn wound repairment.

During long-term clinical practice, the inventor has treated a large number of patients with various skin wounds using the self-prepared pharmaceutical composition, involving about 1000 cases of general surgical dressing changes in clinic and common ward, treatment of emergency skin bruise, medication for burn and scald wound and treatment of bedsore, all of which have achieved effect obviously better than that of traditional wound medication, promoted wound healing, shorten the course of wound treatment, reduced the pain of the patients, saved the cost of medical treatment and relieved the workload of the medical staffs. The sources of the components in pharmaceutical composition of the present invention are all well-known ordinary medicines recorded in Chinese pharmacopoeia. The inventor extracted the pharmaceutically effective components by specific methods according to medical pharmacology in surgical field of combined traditional Chinese and Western medicine, determined the spectrophotometry in practice, and endowed them with a new prescription, whose effect of combined treatment of traditional Chinese and Western medicine in various skin wounds blazes brightly.

Clinical observations in of the wound in 58 cases of burned patients treated with the pharmaceutical composition Formulation 3

1) General Information:

31 cases of clinical patients, who are light burn patients with burn area covering less than 10% of body surface area.

27 cases of hospitalized patients, who are patients with burn area covering 10%-30% of body surface area.

Classified by gender, there are 37 male and 21 female.

Classified by age, there are 12 cases whose age is between 2-14, and 46 cases whose age is over 15.

Classified by depth of burn, there are 43 cases of superficial II degree, 11 cases of deep II degree, 4 cases of III degree or equivalent to III degree.

2) Diagnostic Criteria:

Superficial II degree burn wound, blister on wound skin; and after the blister is cut open, bright red wound and sharp pain.

Deep II degree burn wound, blister or transparent scab on wound skin, red and white wound in the blister or under the scab, light pain.

III degree burn wound, translucent brown scab on wound skin, disappearance of the pain on wound, which may be caused by the deficiency of full thickness skin after infection of II degree burn wound.

3) Treatment Method:

For II degree burn wounds, cut the blister on the day of injury, remove the exudation, and apply the pharmaceutical composition Formulation 3 of the invention onto the of the blister. 24 hours after injury, remove the blister skin and apply the preparation on burn wound, and for III degree burn in small area, apply the preparation on granulation tissue when it grows to the level of the surrounding tissue, both in exposure way.

4) Evaluation Criteria of Therapeutic Effect

Observe the wound development 3-5 days after medicine administration. Observe the superficial II degree burn wound for 8 days, and determine the wound healing tendency according to the condition of the combination of dry scab and wound; observe the deep II degree burn wound for 20 days after medicine administration and determine the wound healing tendency according to the suppuration beneath scab; observe the II degree burn wound with serious infection or III degree burn wound in small area for totally 30 days after continuous removing of necrotic tissue, the granulation tissue growing and reaching the wound surface and multiple medicine administrations, and then determine the wound healing tendency according to the condition of the combination of dry scab and wound. For a few patients whose healing tendency could not be determined, the final treatment result should be the criteria of effect evaluation.

Excellent: superficial II degree burn wound heals and forms scab within 2 weeks, deep II degree burn wound heals and forms scab within 4 weeks, III degree burn wound in small area has dry wound, no fluctuation under the scab and effective control of the granulation wound infection.

Improved: few infections on wound, medicine administration for more than 5 days and prolonged wound healing.

Invalid: incapable of reaching the criteria. Wound healed by skin grafting.

5) Treatment Results (See Table 3):

TABLE 3

Quantification of the treating result on 58 burn patients by using pharmaceutical composition Formulation 3 of the present invention

| Treatment observation time (day) | | | excellent | | improving | | invalid | | Effective |
| --- | --- | --- | --- | --- | --- | --- | --- | --- | --- |
| Superficial II degree burn | deep II degree burn | III degree burn | Case number | excellent rate % | Case number | Improving rate % | Case number | Invalid rate % | rate % |
| 8 | | | 43 | 100 | 0 | | 0 | | 100 |
| | 20 | | 9 | 81.8 | 2 | 18.2 | 0 | | 100 |
| | | 30 | 2 | 50 | 1 | 25 | 1 | 25 | 75 |

Overall effective rate is 98.3%.

Example 4 Medical Cases of Treating Various Skin Wounds During Long-Term Clinical Practice Case 1 Administrating Pharmaceutical Composition Formulation 3 of the Present Invention For superficial II or deep II degree burn and scald wounds, cut out blisters, soak the cotton balls in medicinal liquid of composition, spread the cotton balls gently on the wound, and the liquid may be 1 mm thick. Expose the wound after spreading without dressing and there will be a transparent thin scab formed on the wound within 4-6 hr. In case of more exudation in the wound, apply the medicinal liquid again after 6 hr., apply the medicinal liquid up to three times on the first day. If the wound under the scab is clean and the transparent scab is dry on the second day, then apply the medicinal liquid once only onto the scab. If there is necrotic tissue under the transparent scab, moisturize the transparent scab with saline containing cotton balls and remove the necrotic tissue, and apply the medicinal liquid again. On the third day, when the transparent scab and the wound underneath are clean, continually expose the wound, and apply the medicinal liquid once only on the wound. If the necrotic tissue still exists under the scab, continue with the cleansing and liquid application.

The above treatment of superficial II or deep II degree burn and scald wounds can be healed on schedule and majority of the wounds will not be infected, as long as having the medical consultations without delay.

If the burn and scald wounds damage the full thickness skin or even damage the subcutaneous tissue, they should be treated according to the principle of III degree burn treatment. After granulation tissue grows to the level of normal skin, it is not necessary to make skin graft if the wound size is not big, and apply only the medicinal liquid of the composition. Wound granulation tissue can quickly form transparent scab, the wound swelling subsides and wound gradually heals beneath the scab. Because the wound heals quickly and the granulation tissue does not proliferate repeatedly, the scar from the granulation wound healing after applying the medicinal liquid of the composition of the invention is also relatively soft.

1) Family name: Xu, gender: female, age: 2, address: live in town, date of visit: May 21, 1994. Present illness: The 2 year old girl Xu bumped into the legs of her mother who was then carrying a large bowl of stewed meat from the kitchen to the table. The high-heat broth spilled over the head of the daughter, and scalded her head and face. Therefore she came to the emergency. Examination: swelling and blister on the left ear, left forehead and left cheek, unable to open the left eye. Diagnosis: II degree burns on the left face, and the injured area accounts for about 2% of the body surface area. Treatment: cut out the blister and apply the medicinal liquid of the composition of the invention on the blister skin for twice on the day of injury. On day 2, cut out blister skin, continue applying the medicine on wound. On day 3, the wound was fully covered and protected by the transparent scab, no exudation and secreta. On day 4, the wound was dry, no infection, and medicine administration was stopped. On day 5, swelling on the left head and face and left ear gradually subsided; no pain when touched with cotton swabs. On day 10, the protective scab on the wound began to peel off, showing the primary healing of the wound. The follow-up after half a year showed no scar on face and left ear.

The two skin layers of ear are covered with a layer of cartilage and the surfaces are uneven. In the past, it was difficult to bind up during medication after scalding and the wound could be easily infected, making the treatment afterwards difficult. Applying the composition of the invention on the II degree scalded ear could fully cover the wound on ear without binding up, form protective scab rapidly, effectively eradicate infection and promote healing. II degree scald can become III degree scald once infected, and forms scars in different degrees after healing, leading to disfigurement. As long as the medicinal solution of the composition of the invention is used correctly in the early stage after the injury, there will be no infection and no scab formed on the II degree faciocervical scald.

2) Family name: Yu, gender: male, age: 3, address: live in town, date of admission: Jul. 6, 1995. Present illness: Yu played at home and pulled the thermos bottle on the table down. His neck, chest, abdomen and parts of his perineum and lower limbs was scalded, and he came to the hospital about two hours after the injury. Examination: large blisters were found in many parts of the wound, and blisters were also present on the penis and scrotum. Diagnosis: II degree burns on part of the anterior skin, and the injured area accounts for about 10% of the body surface area. Treatment: in addition to treatments like whole body rehydration, apply the medicinal liquid of the composition of the invention onto the wound with a thickness of about 1 mm and the wound fully exposed. On day 1, cut out the blister skin and apply the medicinal liquid of the composition of the invention on the blister skin, t.i.d. On day 2, remove the blister skin, and apply the medicinal liquid onto the wound, t.i.d. On day 3, the wound had formed the transparent protective scab, under part of which there were red capillary vessels. No necrotic tissue under scab. Continue applying the medicine on wound for once. On day 4, the wound was dry, no secreta was detected by cotton swab, no obvious pain. Stopped the medication and strengthened nutrition. On day 8, the child patient was in good spirits and had a normal diet, and was discharged from the hospital with scab on wound. The result of hospital revisit after another one week showed good scab coverage of the wound, dry and nontender. The result of revisit after one week showed gradually peeled scab skin, red and smooth wound and normal morphology of topical genitals. The wound in perineal region is difficult to bind up and easily gets infected. The exposure treatment will have good effects using the pharmacological composition of the invention.

3) Family name: Mei, gender: male, age: 38, profession: farmer, date of visit: Jul. 25, 1996. Present illness: Mei was driving a small tractor and operating in the field late last night when there was an abrupt mechanical failure and flameout. When he was repairing the machine on the spot by himself, the diesel spray was sprinkled on the high temperature engine cylinder and caused instant flash, and the flame burnt the head, face and neck of the patient. The patient visited the clinic early the next morning. Examination: Oil scattering on head-neck region of the patient, swelling on ears, hair, forehead and face, face beyond recognition, uninjured cornea and respiratory tract. Diagnosis: II degree burns on head-neck, and the injured area accounts for about 8% of the body surface area. Treatment: On day 1, in addition to systemic infusion to prevent infection, use dry cotton swab to lightly remove local oil stains. apply the medicinal liquid of the composition of the invention on the wound, t.i.d. On day 2, remove the blister skin as possible, and apply the medicinal liquid onto the wound, t.i.d. On day 3, most of the wound was covered and protected by the scab and was dry. Only a few small blisters in the hairline and auricle were not eliminated and not absorbed. Continue with the medicine administration of debriding. On day 5, no effusion under scab of the whole wound, swelling has subsided. On day 8, well protection of wound by the scab, and the medication was stopped. On day 14, dry crust, subsided swelling in surrounding tissues, no obvious tenderness. Another 2 weeks later, loose crust with partial exfoliation, good healing of the wound. The follow-up after half a year showed no scar or disfigurement.

4) Family name: Wu, gender: female, age: 6, address: live in countryside, date of visit: Sep. 18, 1997. History of illness: Tripped over and sat down in a porridge pot that had just been moved from the stove to the ground more than 40 days ago, scalded on the whole buttock and the backside of the double thighs. Wu was treated for one day in the local health center and then was transferred to Tongji Hospital in Wuhan and treated there for 40 days. Most of the wounds were healed, but not a large wound on the right buttock, which still needed dressing change every day. According to the patient's farther, the child patient's large wound would not reduce by changing dressing every day in Tongji Hospital. The hospital was going to have reoperation, while the parents were financially exhausted and unable to afford the reoperation. They then asked to be discharged to the local hospital for treatment. When the patient came to our hospital, she had a painful face, poor nutritional status, thin and mild anemia. There is a wound of 8×10 cm in the right buttock. The granulation tissue edema was slightly higher than the surrounding skin. The emergence of these symptoms are because the child patient had been scalded for more than a month, the large skin wound and exudation caused a daily loss of plasma protein and other nutrients and exhausted the body energy. Low body protein makes wound heal very difficult, therefore the wound must be sealed to avoid the loss of nutrients such as proteins from body. Treatment: Give 100 mL of the composition of the invention, demonstrate how to apply the composition with cotton swab, and ask the patient's farther to bring the medicine and cotton swab home and apply to the child patient every day, b.i.d. Expose the wound and apply the medicine for consecutive 5 days. On day 6 of revisit, the swelling granulation tissue was found contracted to the level of the surrounding tissue. The wound was covered with a layer of dry scab, with no liquid under scab. The patient was then told to stop the medication and avoid squeezing the wound. The revisit after another 10 days showed that the wound was still covered by dry scab and the wound under scab improved further. 2 weeks later, the scab skin on the wound gradually peeled off, and the wound under scab formed soft scar and healed.

5) Family name: Zhang, gender: female, age: 17, profession: student of regional health school, date of visit: Jul. 12, 1998. History of illness: Half a month ago, when Zhang was carrying a thermos bottle from the student canteen to the dormitory, wearing shorts, the bottle stopper dropped off unexpectedly and the boiled water flowed out, scalding patient's skin from lateral central part of the right thigh to the lateral malleolus. The patient was receiving daily treatment in school clinic after the injury and came to the clinic two weeks later after back home for the vacation. Examination: Infected wound from the lateral central part of the right thigh to the lateral crus, deep to the subcutaneous tissue. Multiple yellow-green purulent necrotic tissues on the wound and were difficult to be removed. Diagnosis: II degree scald with infection. Treatment: Try to remove the necrotic tissues on the wound, apply the pharmaceutical composition of the invention mixed with gentamycin and chloramphenicol onto the wound. On the first day, apply every 6 hr.; q.i.d. on day 2 and day 3. The patient told that the local pain on wound reduced significantly during the revisit on day 4. Examination showed that most of the wound was dry, with few empyema under scab. Rinse and moisturize the local scab with pus with saline containing cotton balls, and remove the empyema and necrotic tissue under the scab, apply the above medicinal liquid. After the same treatment for another consecutive 3 days, the swelling on patient's wound gradually subsided and covered by dry scab. The wound under scab was clean and no empyema. The patient was asked to stop the medication, avoid pressing, touching or scratching the scab skin on wound, and wait until the scab to peel off by itself.

Case 2 Administrating Pharmaceutical Composition Formulation 2 of the Present Invention For skin contusion and skin wound after surgical incision suture, apply the medicinal liquid of the composition of the invention after wound cleansing and wiping dry. Expose the wound of skin contusion without dressing after medicine administration. If a thin layer of sterile gauze is used, it is for the purpose of isolating wound from the cloth.

For skin contusion or suture wound after incision, or after stich removing, applying the medicinal liquid of the composition of the invention can prevent bacterial invasion of wounds from outside.

1) Family name: Yu, gender: male, age: 34, profession: teacher, date of visit: Aug. 26, 1998. Present illness: Yu was riding a motorcycle when it fell on the cement road. It scratched the right side of the patient's body, so he comes to the emergency of the hospital. Examination: extensive skin abrasions on patient's right side body from the face, hand, elbow, waist abdomen, and lateral thigh and crus. Part of the wound was a mass of bleeding flesh. No fracture of the whole body and no visceral injuries were seen in the chest and abdomen. Diagnosis: Extensive skin and soft-tissue contusion on right-side body. Treatment: Continue to observe the injury of the whole body viscera and bones, inject Tetanus Antitoxin. Apply the medicinal liquid of the composition of the invention on wound after cleansing. t.i.d., on day 1. On day 2, the scab formed scab and the pain was relieved, apply the medicine, b.i.d. On day 3, wound pain reduced significantly, scab was dry and nontender with light touch. Stop the medication. After 10 days of resting, all the wounds healed.

2) Family name: Wang, gender: male, age: 41, profession: staff member, date of visit: Sep. 2, 2002. Present illness: Wang was injured by the sudden burst of tempered glass door during shower last night. The right side body of the patient was stabbed by broken glass and gushed blood. After dressing and other treatments in local surgical emergency, he visited the clinic. Treatment: remove the dressing and apply on the wound the composition of the invention. b.i.d., on day 1. On day 2, the wound was fully covered by dry scab. Apply the medicine again on the dry scab. On day 3, the wound was nontender with light touch. The patient stopped the medication and achieved primary healing.

3) Family name: Li, gender: male, age: 68, profession: retired staff member, date of visit: Aug. 21, 2005. Present illness: Li got up to urinate and hit the edge of a plastic bucket last night. The anterior skin on right crus was injured. Examination: a skin flap with a size of about 1×1.5 cm was raised on the tibialis anterior skin of the right crus. Skin flap curled up and turned blue. Treatment: Preventive injection of TAT. Apply composition of the invention on wound after regular cleansing. B.i.d., on day 1. Q.i.d., on day 2 and day 3. On day 4, the wound had formed dry scab to the level of the surrounding skin, had no swelling on wound edge, and was nonterder with light touch. The patient was asked to stop the medication and avoid touch wound. 15 days later, the scab skin was loose. 18 days later, scab skin peeled off and the wound was almost flat and no scar, left only pale gray pigmentation. The follow-up after 18 months showed subsided pigmentation and no scar on the wound.

Case 3 Administrating Pharmaceutical Composition Formulation 1 of the Present Invention For infectious skin disease, such as the granulation tissue wound after ulceration of impetigo, yellow fluid ulcer, leg ulcer, furuncle and carbuncle, cleanse and wipe dry the wound surface or granulation tissue wound with saline containing cotton ball and apply the medicinal liquid of the composition of the invention. The infection on sore wound can be rapidly controlled and recovered.

1) Family name: Zhu, gender: male, age: 5, address: live in countryside, date of visit: Sep. 6, 1996. History of illness: 10 days with head impetigo. Chlortetracycline ointment was used on the sore at home but failed to control the sore flow. Examination: Hair had already been cut short and stuck together, with left side more serious and right face and forehead having purulent scar. Body temperature: 37.1° C., whole body in good condition. Treatment: wash out the purulent scar on face and forehead with saline, cut out the grown hair, wipe dry wound with sterile gauze, and apply the composition of the invention (0.25 g of chloramphenicol per 100 mL). The medicine was brought home and applied t.i.d. on day 1, b.i.d. on day 3. Revisit on day 3 showed the impetigo wound on face and head formed scab, no yellow fluid reflow, and the infection was controlled. The patient was asked to apply medicine for two more time before stop the medication. Revisit after another 3 days showed that wound was covered well by scab skin, had no inflammatory swelling around the base and was nontender. The wound gradually healed completely.

2) Family name: Zhang, gender: female, age: 83, address: live in town, date of admission: Nov. 11, 2002. Present illness: Zhang fell at home and caused left femoral neck fracture. The patient was admitted into the ICU ward after bone surgery fixation, but suffered bedsore on the sacrum after one week in bed. Routine bedsore nursing change did not control the infection of bedsore. Treatment: cleanse and wipe dry the bedsore wound, apply the pharmaceutical composition of the invention and expose the wound. Apply the medicine, t.i.d., on day 1. On day 2, bedsore wound formed scab with no secretion. Continue to apply the medicine, b.i.d., for consecutive 5 days. The bedsore wound remained covered by scab and dry. Apply the medicinal liquid of the composition on time after wiping away the scab from the bedding. The blood circulation of the wound improved and the wound area decreased. The wound gradually healed in two weeks.

3) Family name: Sun, gender: male, age: 56, profession: farmer, date of visit: Sep. 11, 1998. Present illness: ache on left upper back 4 days ago and the pain aggravated day by day. On the fifth day after onset, the pain was unbearable, and the patient came to the hospital for treatment. Examination: a skin flap with a size of about 1×1.5 cm was raised on the tibialis anterior skin of the right crus. Skin flap curled up and turned blue. Treatment: body temperature 38.2° C., red, swelling, hot and sclerosis on the right upper back, central subcutaneous yellow pus can be seen, obvious tenderness, unbroken and no local fluctuation. Diagnosis: cellulitis on left upper back (carbuncle on the back). Treatment: systemic use of tetracycline 0.5, oral administration by every 6 hr. for consecutive 3 days. Perform local incision in " ╫ " shape under local anesthesia to open pus cavity and make decompression drainage. Soak the sterile gauze strip in the medicinal liquid of the composition of the invention and place in the incision as drainage strip. Change dressing, q.i.d. On day 2, local pain reduced significantly, body temperature 37.3° C. On day 4, body temperature 36.8° C., no local pain without touching, significantly subsided swelling and reduced secretion from incision drainage. On day 7, no purulent secretion in incision and no need of drainage. Two days after changing to pressure dressing, the incision grew flat. Expose the wound and apply medicinal liquid of the composition, bid, for 2 days. The wound formed protective dry scab, and the wound under scab healed gradually.

INCORPORATION BY REFERENCE

Every of the patent documents and scientific articles referred to herein are incorporated by reference in their entirety for all purposes.

EQUIVALENTS

The invention may be embodied in other specific forms without departing from the spirit or essential characteristics thereof. The foregoing examples are therefore to be considered in all respects illustrative rather than limiting on the invention described herein. Scope of the invention is indicated by the appended claims rather than by the foregoing description, and all changes that come within the meaning and the range of equivalency of the claims are intended to be embraced therein.

The invention claimed is:

1. A liquid-state topical pharmaceutical composition for treating skin wounds comprising:
  (i) glycerol,
  (ii) water,
  (iii) 1,2-propanediol,
  (iv) laurocapram or decyl methyl sulfoxide,
  (v) a pharmaceutically effective component extracted by glycerol and water from at least one ingredient selected from the group consisting of Astragali Radix, Angelicae Sinensis Radix, Salviae Miltiorrhizae Radix et Rhizoma, Paeoniae Radix Rubra, Coptidis Rhizoma, Scutellariae Radix, Phellodendri Chinensis Cortex, Gardeniae Fructus, Ampelopsis Radix, Ilex purpurea Hassk, Bletillae Rhizoma, Glycyrrhizae Radix et Rhizoma, and
  (vi) a pharmaceutically effective component extracted by 1,2-propanediol from at least one ingredient selected from the group consisting of Olibanum, Myrrha, Draconis Sanguis and Catechu;
  wherein the glycerol is present in the composition in an amount of 80% to 90% by volume with respect to a total volume of the liquid-state topical pharmaceutical composition;
  the water is present in the composition in an amount of 3% to 8% by volume with respect to a total volume of the liquid-state topical pharmaceutical composition;
  the 1,2-propanediol is present in the composition in an amount of 6% to 15% by volume with respect to a total volume of the liquid-state topical pharmaceutical composition; and
  the laurocapram is present in the composition in an amount of 0.2% to 2% by volume with respect to a total volume of the liquid-state topical pharmaceutical composition; or the decyl methyl sulfoxide is present in the composition in an amount of 1% to 4% by volume with respect to a total volume of the liquid-state topical pharmaceutical composition.

2. The pharmaceutical composition of claim 1, comprising one or more of the following:
  1) a content of Astragali Radix in the composition is 10-30 g/L;
  2) a content of Angelicae Sinensis Radix in the composition is 5-20 g/L;
  3) a content of Salviae Miltiorrhizae Radix et Rhizoma in the composition is 5-20 g/L;
  4) a content of Paeoniae Radix Rubra in the composition is 5-20 g/L;
  5) a content of Coptidis Rhizoma in the composition is 5-20 g/L;
  6) a content of Scutellariae Radix in the composition is 5-20 g/L;
  7) a content of Phellodendri Chinensis Cortex in the composition is 5-20 g/L;
  8) a content of Gardeniae Fructus in the composition is 5-20 g/L;
  9) a content of Ampelopsis Radix in the composition is 5-20 g/L;
  10) a content of Ilex purpurea Hassk in the composition is 5-20 g/L;
  11) a content of Bletillae Rhizoma in the composition is 5-20 g/L;
  12) a content of Glycyrrhizae Radix et Rhizoma in the composition is 5-15 g/L;
  13) a content of Olibanum in the composition is 3-10 g/L;
  14) a content of Myrrha in the composition is 3-10 g/L;
  15) a content of Draconis Sanguis in the composition is 3-10 g/L; and
  16) a content of Catechu in the composition is 3-10 g/L.

3. The pharmaceutical composition of claim 1, wherein the pharmaceutical composition further comprises gentamicin and chloramphenicol.

4. The composition of claim 1 wherein the skin wound comprises one selected from the group consisting of burn wound, scald wound, skin contusion wound, suture wound after incision, bedsore wound, skin infection wound, and granulation tissue wound.

5. The pharmaceutical composition of claim 1, wherein the content of Astragali Radix in the composition is 10-15 g/L.

6. The pharmaceutical composition of claim 1, wherein the content of Angelicae Sinensis Radix in the composition is 6-8 g/L.

7. The pharmaceutical composition of claim 1, wherein the content of Salviae Miltiorrhizae Radix et Rhizoma in the composition is 8-10 g/L.

8. The pharmaceutical composition of claim 1, wherein the content of Paeoniae Radix Rubra in the composition is 8-10 g/L.

9. The pharmaceutical composition of claim 1, wherein the content of Coptidis Rhizoma in the composition is 6-8 g/L.

10. The pharmaceutical composition of claim 1, wherein the content of Scutellariae Radix in the composition is 6-8 g/L.

11. The pharmaceutical composition of claim 1, wherein the content of Phellodendri Chinensis Cortex in the composition is 6-8 g/L.

12. The pharmaceutical composition of claim 1, wherein the content of Gardeniae Fructus in the composition is 6-8 g/L.

13. The pharmaceutical composition of claim 1, wherein the content of Ampelopsis Radix in the composition is 8-10 g/L.

14. The pharmaceutical composition of claim 1, wherein the content of Ilex purpurea Hassk in the composition is 8-10 g/L.

15. The pharmaceutical composition of claim 1, wherein the content of Bletillae Rhizoma in the composition is 8-10 g/L.

16. The pharmaceutical composition of claim 1, wherein the content of Glycyrrhizae Radix et Rhizoma in the composition is 8-10 g/L.

\* \* \* \* \*